United States Patent
Baik et al.

(10) Patent No.: US 7,247,325 B2
(45) Date of Patent: Jul. 24, 2007

(54) CRUDE DRUG COMPOSITIONS AND THE PROCESS FOR PREPARING THEM

(75) Inventors: Soon-Ok Baik, Daejeon (KR); You-Hui Lee, Seoul (KR); Hyun-Kyoung Kim, Daejeon (KR); Young-Sook Kim, Daejeon (KR)

(73) Assignee: K.T.& G. Corporation (KR)

( * ) Notice: Subject to any disclaimer, the term of this patent is extended or adjusted under 35 U.S.C. 154(b) by 0 days.

(21) Appl. No.: 11/408,126

(22) Filed: Apr. 19, 2006

(65) Prior Publication Data

US 2006/0257506 A1 Nov. 16, 2006

Related U.S. Application Data

(62) Division of application No. 10/734,916, filed on Dec. 11, 2003, now abandoned.

(30) Foreign Application Priority Data

Dec. 12, 2002 (KR) .................. 10-2002-0079086
Dec. 1, 2003 (KR) .................. 2003-0086324

(51) Int. Cl.
*A61K 36/23* (2006.01)
*A61K 36/82* (2006.01)

(52) U.S. Cl. .................. 424/729; 424/735; 424/736; 424/754

(58) Field of Classification Search .................. None
See application file for complete search history.

*Primary Examiner*—Susan Hoffman
(74) *Attorney, Agent, or Firm*—Anderson Kill & Olick, PC

(57) ABSTRACT

The present invention provides a crude drug composition comprising extracts of radish and tea leaf and additionally comprising an extract extracted from at least one crude drug selected from a group consisting of *Daucus carota* var *sativa, Aurantii nobilis* Pericapium, *Aurantii immatri* Pericarpium, *Ficus carica* L., *Allium cepa* L., *Mume Fructus* and *Prunus armeniaca*. Inventive composition induces the functional activation of intestine in the charcoal-administered animal model experiment and constipation-induced animal model and improves the constipation by activating mucus secretion in the intestine. And the composition is confirmed to inhibit the growth of intestinal harmful bacteria without affecting the growth of beneficial bacteria. Therefore, the crude drug composition of the present invention may be useful for the pharmaceutical composition and health care food for preventing, alleviating and treating intestinal disease and constipation.

2 Claims, 8 Drawing Sheets

CRUDE DRUG COMPOSITIONS AND THE PROCESS FOR PREPARING THEM

CROSS REFERENCE TO RELATED APPLICATION

This application is a Divisional Application of U.S. Ser. No. 10/734,916, filed on Dec. 11, 2003, now abandoned.

This application is an international patent application, claiming the benefit under 35 USC § 111 (a) of Korean Patent Application No. 10-2002-79086 filed on Dec. 12, 2002 and Korean Patent Application No. 10-2003-86324 filed on Dec. 1, 2003.

BACKGROUND OF THE INVENTION

1. Field of Invention

The present invention relates to a composition for prevention and treatment of intestinal disease and constipation. More specifically, the present invention provides the composition essentially comprising extracts of radish and tea leaf and additionally comprising an extract extracted from crude drug selected from the group consisting of *Daucus carota* var *sativa*, *Aurantii nobilis* Pericapium, *Aurantii immatri* Pericarpium, *Ficus carica* L., *Allium cepa* L., *Mume Fructus* and *Prunus armeniaca* and the process for preparing them.

2. Background

Recently, the number of patient suffering from constipation has been increased with modem high fat and high protein meal pattern and the syndrome of constipation is characterized in anorexia, skin aging, headache, acne, skin rash, hemorrhoids, colon cancer, which are caused by absorbed toxic substance exuded from feces not yet discharged through intestinal peristaltic movement. It has been reported that constipation is caused by weak peristaltic movement or defecation reflex leading to hindrance in propagation, and the criteria for judging constipation is in case that the number of bowel movement is less than twice a week and the mass of feces is less than 35 g.

There have been tried to alleviate constipation or to stimulate peristaltic movement by using therapeutic method such as exercise as a first choice and various drug such as herbal laxative containing anthraquinone derivatives isolated from senna folium, rhei rhizoma (*Rheum undulatum*) and the like or food such as dietary fiber as a second choice till now. However, the laxative drug has limit such as the caution not to be administered everyday or during the pregnancy because of its high irritancy.

Common functional food material for improving constipation have been manufactured by using dietary fiber, sea tangle (*Laminaria japonica*), yakon, *Saururus chinensis*, tea of *Cassia tora* seed, tea of *Malva verticillata* seed, aloe, sea weed and so on, however, the efficacy of those have not been substantiated scientifically yet till now.

Intestinal disease includes chronic/acute gastroenteritis and food poisoning caused by bacteria such as *E. coli*, salmonella and the like.

In particular, *Salmonella typhimurium* DT104 has been reported to show multiple antimicrobial resistance against several antibiotics such as ampicillin, chloramphenicol, streptomycin, sulfonamides and tetracycline. Such an antibiotic-resistance bacteria makes it difficult to treat infectious disease, and propagates the antibiotic resistant-gene to other bacteria through transformation. Furthermore, *Salmonella typhimurium* DT104 having additional resistance to trimethoprim and ciprofloxacin was reported in England.

Recently, *Escherichia coli* O157:H7 broke out mass food poisoning in U.S. and Japan accompanying hemolytic uremia and hemolytic colitis in patients.

There have been lots of trial to investigate effective drug or health food to treat or alleviate constipation and to regulate intestinal microflora from natural products till now.

It has been reported that *Raphanus sativus* L. and *Brassia Lap.* belonged to Cruciferae, contains glucose, fructose, coumaric acid, caffeic acid, ferulic acid, phenylpyruvic acid, gentidin acid, hydroxy benzoic acid and several amino acids in the radix thereof and the alcoholic extract of the radix shows anti-microbial and anti-fungal activity (Chung. B. S. and Shin M. K.; *HyanghakDaeSaJeon*, Youngrim Press, pp 582-584, 1998).

It has been reported that the young tender leave of *Camellia sinensis* belonged to Theaceae contains 1-5% purine alkaloid and caffeine besides theobrornine, theophylline and xanthine. Most of tannin in tea leaf is galloyl-l-epigallocatechol together with several amount of caffeine, which shows the antibiotic and vitamin P-like activity, CNS excitation, momory enhancing activity, vasodilatory and diuretic activity due to xanthine derivatives such as caffeine and theophylline (Chung. B. S. and Shin M. K.; *HyanghakDaeSaJeon*, Youngrim Press, pp 403-405, 1998). The young leaves of *Camellia sinensis* may be processed as various teas such as black tea, oolong tea, Tien-Guan-In tea, Boe-Jong tea, green tea according to their respective processes, for example, post-fermentation, fermentation, half-fermentation, non-fermentation and the like.

*Daucus carota* L. var. *sativa* DC. belonged to Umbelliferae contains various carotenoids such as $\alpha$-, $\beta$-, $\gamma$-, $\epsilon$-carotene, lycopene, phytofluene, and vitamin $B_1$, $B_2$ and anthocyanidin etc, which has been used to strengthen the internal organs such as heart, stomach and spleen, and to treat dyspepsia.

*Aurantii nobilis* Pericapium is a dried peel of mature fruit of *Citrus unshiu* MARCOR. belonged to Rutaceae, while *Aurantii immatri* Pericapium is a dried peel of immature one and contain limonene, flavonoid glycoside, hesperidin, citric acid, naringin, aspartic acid and so on. It has been known to show the strengthening activity of the internal organs such as heart, stomach and spleen, the dyspepsia-treating activity, antitussive activity, and type I anti-allergic activity.

The fruit of *Ficus carica* L belonged to Moraceae, contains approximately 10% saccharides such as glucose, fructose and the like, organic acids such as malic acid, citric acid, benzaldehyde, various enzymes such as ficin, lipase, amylase and oxydase, fiber and protein. It has been used for treating hypogalactia, anorexia and detoxifying agent.

*Allium cepa* L. belonged to Liliaceae, contains thiol, dimethyl disulfide, dially-disulfide and dially thioether, thiosulfinic acid salt and malic acid, of which root and leaf contain coumaric acid, caffeic acid, ferulic acid and sinapic acid and have pharmacological activity such as lowering blood cholesterol and decreasing fibrin solubility.

*Mume Fructus*, a steamed and dried immature fruit of *Prunus mume* belonged to Amygdalaceae contains citric acid, malic acid, sitosterol and oleanolic acid, and shows anti-bacterial, anti-fungal activity and detoxifying activity.

A fruit of *Prunus armeniaca* L. belonged to Amygdalaceae contains citric acid, $\beta$-carotene and essential oil such as myrcene, limonene, p-cymene and terpinolene and it is reported that it has been used for treating asthma, bronchitis and acute hepatitis.

There have been several reports on above described herbs or crude drug.

For example, *Raphanus sativus* showed anti-cancer activity (*Adv. Exp. Med. Biol.*, 289, pp 153-163, 1991; *Am. J. Epidemiol.*, 144, pp 1015-1025, 1996) and liver detoxificating activity (*Biosci. Biotechnol. Biochem.*, 59, pp 1882-1886, 1995; *Arch. Biochem. Biophys.*, 316, pp 797-802, 1995).

Korea patent publication No. 180452 discloses the health nutrient composition for improving constipation and scavenging feces smell comprising *Aloe arborescens*, a seed extract of *Cassia tora*, a seed extract of *Malva verticillata* and green tea leaves.

Korea patent publication No. 149389 discloses crude drug composition comprising dried mandarin orange peel, ginseng, fruit of *Schizandra chinensis*, alum, *Glycyrrhiza uralensis*, seed of apricot and fruit of *Lycium chinensis* for treating constipation.

U.S patent application Ser. No. 2002-0068097 discloses a composition consisting essentially of extracts of *Paeonia lactiflora*, *Atractylodes macrocephala*, *Citrus reticulata* and *Saposhnikovia divaricata* for treatment of bowel disorders.

The disclosures of which above cited literatures or patents is incorporated herein by reference.

The inventors of the present invention have intensively carried out the scientific investigation concerning pharmacological effects and its mechanism of action, in particular a treating activity of intestinal disease and constipation or inhibiting activity of intestinal microbial growth.

As a result of the investigation, the inventors have discovered that the inventive extract of crude drug combination shows novel pharmacological effects, especially, its treating or alleviating activity for intestinal disease or constipation confirmed by various in vitro, in vivo and clinical experiments and they have finally completed the present invention.

SUMMARY OF THE INVENTION

According to one aspect of the present invention, the present invention provides a crude drug composition essentially comprising the extract of radish and tea leaf for treating and preventing intestinal disease and constipation.

The present invention provides a pharmaceutical composition essentially comprising above-mentioned crude drug as an active ingredient in an effective amount to treat and prevent intestinal disease and constipation, together with a pharmaceutically acceptable carrier.

The present invention also provides a use of above-mentioned crude drug composition for the preparation of pharmaceutical composition to treat and prevent intestinal disease and constipation in mammal or human.

The present invention also provides a method for treating or preventing intestinal disease and constipation, comprising administering to said mammal or human an effective amount of above-mentioned crude drug, together with a pharmaceutically acceptable carrier thereof.

The present invention also provides a health care food comprising above-mentioned crude drug for preventing or alleviating intestinal disease and constipation, together with a sitologically acceptable additive.

The present invention still provides the process for preparing the above-mentioned crude drug composition.

Disclosure of the Invention

Accordingly, it is an object of the present invention to provide a pharmaceutical composition essentially comprising an extract of radish and tea leaf as an active ingredient in an effective amount to treat and prevent intestinal disease and constipation, together with a pharmaceutically acceptable carrier thereof.

The term "radish" disclosed herein comprises the root of *Raphanus sativus* L., *Brassia* Lap. and the like.

The term "tea leaf" disclosed herein comprises the processed tea leaf including unfermented and fermented leaf of *Camellia sinensis* or other similar species thereof such as green tea leaf, oolong tea leaf, black tea leaf, Pu-erh tea leaf, Tien-Guan-In tea leaf, Boe-Jong tea leaf and the like.

It is another object of the present invention to provide a pharmaceutical composition comprising an extract extracted from at least one crude drug selected from the group consisting of *Daucus carota* var *sativa*, *Aurantii nobilis* Pericapium, *Aurantii immatri* Pericarpium, *Ficus carica* L., *Allium cepa* L., *Mume Fructus* and *Prunus armeniaca*, besides above-mentioned essential crude drug for preventing and treating intestinal disease and constipation, together with a pharmaceutically acceptable carrier thereof.

In accordance with one aspect of the present invention, there provided a pharmaceutical composition essentially comprising an extract of crude drug combination consisting of radish, tea leaf, *Daucus carota* var *sativa*, *Aurantii nobilis* Pericapium, *Aurantii immatri* Pericarpium, *Ficus carica* L., *Allium cepa* L. and *Mume Fructus*.

In accordance with another aspect of the present invention, there provided a pharmaceutical composition essentially comprising an extract of crude drug combination consisting of radish, tea leaf, *Daucus carota* var *sativa*, *Aurantii nobilis* Pericapium, *Aurantii immatri* Pericarpium, and *Allium cepa* L.

In accordance with another aspect of the present invention, there provided a pharmaceutical composition essentially comprising an extract of crude drug combination consisting of radish, tea leaf, *Daucus carota* var *sativa*, *Aurantii nobilis* Pericapium and *Aurantii immatri* Pericarpium.

In accordance with another aspect of the present invention, there provided a pharmaceutical composition essentially comprising an extract of crude drug combination consisting of radish, tea leaf, *Daucus carota* var *sativa*, *Aurantii nobilis* Pericapium, *Aurantii immatri* Pericarpium, *Ficus carica* L. and *Mume Fructus*.

In accordance with still another aspect of the present invention, there provided a pharmaceutical composition essentially comprising an extract of crude drug combination consisting of radish, tea leaf, *Daucus carota* var *sativa*, *Aurantii nobilis* Pericapium, *Aurantii immatri* Pericarpiumn, *Ficus carica* L., *Allium cepa* L., *Mume Fructus* and *Prunus armeniaca*.

Additionally, it is another object of the present invention to provide a pharmaceutical composition essentially comprising an extract of crude drug combination consisting of radish, tea leaf, *Daucus carota* var *sativa*, *Aurantii nobilis* Pericapium, *Aurantii immatri* Pericarpium, *Ficus carica* L., *Allium cepa* L., *Mume Fructus* and *Prunus armeniaca*, preferably with the ratio of 1~2:0.1~1:1~2:0.01~1:0.01~1:0.01~1:0.1~2:0.01~1:0.01~1

The crude drugs which can be used in the present invention, include the same genus plants which would be apparent to those skilled in the art and have been used for identical or similar purpose and can be substituted for the prevention and treatment of intestinal disease and constipation.

Inventive crude drug can be used in the form of pulverized form thereof, extracted form thereof or dried extract form thereof.

Above described intestinal disease comprises all the intestinal disease caused by microorganism such as *Escherichia coli* and *Salmonella typhimurium*, food poisoning, acute enteritis, acute diarrhea and the like.

The pharmaceutical composition for treating intestinal diseases and constipation could contain about 0.01 to 80 w/w %, preferably 1 to 50 w/w % of the above described extract of present invention based on the total weight of the composition.

An inventive crude drug extract may be prepared in accordance with the following preferred embodiment.

For the present invention, above crude drug extract can be prepared by following procedure;

(1) Crude drugs, i.e., radish, tea leaf, *Daucus carota* var *sativa, Aurantii nobilis* Pericapium, *Aurantii immatri* Pericarpium, *Ficus carica* L., *Allium cepa* L., *Mume Fructus* and *Prunus armeniaca* are washed, cut into small pieces and dried. Each dried crude drug is mixed with 5 to 20-fold, preferably, 10 to 12-fold volume, of distilled water, alcohols such as methanol, ethanol and the like, or the mixtures thereof; is heated at the temperature ranging from 70 to 120° C., preferably above 90° C., for the period ranging from 1 to 5 hours, preferably 2 to 3 hours with 1 to 5 times to obtain an crude extract therefrom.

Above crude extract is further lyophilized or dried under reduced pressure, preferably lyophilized to obtain a dried extract of each crude drug.

(2) Each dried crude drug extract is centrifuged, filtered, concentrated at the temperature ranging from 40 to 80° C. and mixed them with appropriate ratio (w/w), preferably 1~2:0.1~1:1~2:0.01~1:0.01~1:0.01~1:0.1~2:0.01~1:0.01~1. Further, other addable crude drugs with appropriate ratio are mixed therewith and all the mixture thereof is poured to 5 to 20-fold, preferably, 10 to 15-fold volume of distilled water, alcohols such as methanol, ethanol and the like, or the mixtures thereof, preferably distilled water or the mixture of ethanol and water; is heated at the temperature ranging from 70 to 120° C., preferably above 90° C., for the period ranging from 1 to 5 hours, preferably 2 to 3 hours with 1 to 5 times; and is lyophilized or dried under reduced pressure, preferably lyophilized to obtain a pulverized form of crude drug composition.

It is another object of the present invention to provide a process for preparing crude drug composition comprising the step consisting of; (i) washing, cutting into small pieces and smashing or drying crude drugs, i.e., radish, tea leaf, *Daucus carota* var *sativa, Aurantii nobilis* Pericapium, *Aurantii immatri* Pericarpium, *Ficus carica* L., *Allium cepa* L., *Mume Fructus* and *Prunus armeniaca*; (ii) mixing dried or juicy form of crude drugs with appropriate ratio (w/w) with 5 to 20-fold of distilled water, alcohols such as methanol, ethanol and the like, or the mixtures thereof; (iii) heating the mixture at the temperature ranging from 70 to 120° C. for the period ranging from 1 to 5 hours with 1 to 5 times; (iv) lyophilizing or drying the extract under reduced pressure to obtain an pulverized form of crude drug composition.

In accordance with another aspect of the present invention, there provided a crude drug composition of radish, tea leaf, *Daucus carota* var *sativa, Aurantii nobilis* Pericapium, *Aurantii immatri* Pericarpium, *Ficus carica* L., *Allium cepa* L., *Mume Fructus* and *Prunus armeniaca* with a ratio of 1~80%:1~80%:1~80%:0.1~20%:0.1~20%:1~50%:1~50%: 0.5~10:1~50% based on the total weight of the composition. In particular, radish, *Daucus carota* var *sativa* or *Allium cepa* L. among them can be used in the juicy form preferably.

In accordance with another aspect of the present invention, there provided a crude drug combination which can add or remove appropriately another crude drugs and increase or decrease composition ratio of crude drugs within the limit which can keep their efficacy.

It is an object of the present invention to provide a use of a crude drug composition essentially comprising extracts of radish and tea leaf for the preparation of therapeutic agent for treatment and prevention of intestinal disease and constipation in human or mammal.

It is an object of the present invention to provide a method of treating or preventing intestinal disease and constipation in a mammal comprising the step of administering to said mammal an effective amount of crude drug essentially comprising extract of radish and tea leaf, together with a pharmaceutically acceptable carrier thereof.

Above-mentioned essential crude drug can additionally comprises an extract extracted from at least one crude drug selected from the group consisting of *Daucus carota* var *sativa, Aurantii nobilis* Pericapium, *Aurantii immatri* Pericarpium, *Ficus carica* L., *Allium cepa* L., *Mume Fructus* and *Prunus armeniaca* for preventing and treating intestinal disease and constipation.

The inventive composition may additionally comprise conventional carrier, adjuvants or diluents in accordance with a using method. It is preferable that said carrier is used as appropriate substance according to the usage and application method, but it is not limited. Appropriate diluents are listed in the written text of Remington's Pharmaceutical Science (Mack Publishing co, Easton Pa.).

Hereinafter, the following formulation methods and excipients are merely exemplary and in no way limit the invention.

The crude drug composition according to the present invention can be provided as a pharmaceutical composition containing pharmaceutically acceptable carriers, adjuvants or diluents, e.g., lactose, dextrose, sucrose, sorbitol, mannitol, xylitol, erythritol, maltitol, starches, acacia rubber, alginate, gelatin, calcium phosphate, calcium silicate, cellulose, methyl cellulose, polyvinyl pyrrolidone, water, methylhydroxy benzoate, propylhydroxy benzoate, talc, magnesium stearate and mineral oil. The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a patient by employing any of the procedures well known in the art.

For example, the compositions of the present invention can be dissolved in oils, propylene glycol or other solvents which are commonly used to produce an injection. Suitable examples of the carriers include physiological saline, polyethylene glycol, ethanol, vegetable oils, isopropyl myristate, etc., but are not limited to them. For topical administration, the extract of the present invention can be formulated in the form of ointments and creams.

Pharmaceutical formulations containing crude drug composition may be prepared in any form, such as oral dosage form (powder, tablet, capsule, soft capsule, aqueous medicine, syrup, elixirs pill, powder, sachet, granule), or topical preparation (cream, ointment, lotion, gel, balm, patch, paste, spray solution, aerosol and the like), suppository, or sterile injectable preparation (solution, suspension, emulsion).

The crude drug composition of the present invention in pharmaceutical dosage forms may be used in the form of their pharmaceutically acceptable salts, and also may be used alone or in appropriate association, as well as in combination with other pharmaceutically active ingredients.

The desirable dose of the inventive composition varies depending on the condition and the weight of the subject, severity, drug form, route and period of administration, and may be chosen by those skilled in the art. However, in order to obtain desirable effects, it is generally recommended to administer at the amount ranging 0.01-10 g/kg, preferably, 0.1 to 1 g/kg by weight/day of the inventive composition of the present invention. The dose may be administered in a single or multiple doses per day.

The pharmaceutical composition of present invention can be administered to a subject animal such as mammals (rat, mouse, domestic animals or human) via various routes. All modes of administration are contemplated, for example, administration can be made orally, rectally or by intravenous, intramuscular, subcutaneous, intracutaneous, intrathecal, epidural or intracerebroventricular injection.

It is still another object of the present invention to provide a health care food comprising above crude drug composition essentially comprising the extract of radish and tea leaf, together with a sitologically acceptable additive for preventing and improving intestinal disease and constipation.

It is another object of the present invention to provide a health care food comprising an extract extracted from at least one crude drug selected from the group consisting of *Daucus carota* var *sativa*, *Aurantii nobilis* Pericapium, *Aurantii immatri* Pericarpium, *Ficus carica* L., *Allium cepa* L., *Mume Fructus* and *Prunus armeniaca*, besides above-mentioned essential crude drug composition for preventing and improving intestinal disease and constipation.

In accordance with one aspect of the present invention, there provided a health care food essentially comprising the extract of crude drug combination consisting of radish, tea leaf, *Daucus carota* var *sativa*, *Aurantii nobilis* Pericapium, *Aurantii immatri* Pericarpium, *Ficus carica* L., *Allium cepa* L. and *Mume Fructus*.

In accordance with another aspect of the present invention, there provided a health care food essentially comprising the extract of crude drug combination consisting of radish, tea leaf, *Daucus carota* var *sativa*, *Aurantii nobilis* Pericapium, *Aurantii immatri* Pericarpium and *Allium cepa* L.

In accordance with another aspect of the present invention, there provided a health care food essentially comprising the extract of crude drug combination consisting of radish, tea leaf, *Daucus carota* var *sativa*, *Aurantii nobilis* Pericapium and *Aurantii immatri* Pericarpium.

In accordance with another aspect of the present invention, there provided a health care food essentially comprising the extract of crude drug combination consisting of radish, tea leaf, *Daucus carota* var *sativa*, *Aurantii nobilis* Pericapium, *Aurantii immatri* Pericarpium, *Ficus carica* L. and *Mume Fructus*.

In accordance with still another aspect of the present invention, there provided a health care food essentially comprising the extract of crude drug combination consisting of radish, tea leaf, *Daucus carota* var *sativa*, *Aurantii nobilis* Pericapium, *Aurantii immatri* Pericarpium, *Ficus carica* L., *Allium cepa* L., *Mume Fructus* and *Prunus armeniaca*.

Additionally, it is another object of the present invention to provide a health care food essentially comprising the extract of crude drug combination consisting of radish, tea leaf, *Daucus carota* var *sativa*, *Aurantii nobilis* Pericapium, *Aurantii immatri* Pericarpium, *Ficus carica* L., *Allium cepa* L., *Mume Fructus* and *Prunus armeniaca*, preferably with a ratio of 1~2:0.1~1:1~2:0.01~1:0.01~1:0.01~1:0.1~2: 0.01~1:0.01~1.

The health care food for preventing and alleviating intestinal diseases and constipation could contain about 0.01 to 80 w/w %, preferably 1 to 50 w/w % of the above crude drug combination of present invention based on the total weight of the composition.

Also, the present invention provides a composition of the health care food for preventing and alleviating intestinal disease comprising the extracts of crude drug wherein radish 1 to 80% by weight, tea leaf 1 to 80% by weight, *Daucus carota* var *sativa* 1 to 80% by weight, *Aurantii nobilis* Pericapium 0.1 to 20% by weight, *Aurantii immatri* Pericarpium 0.1 to 20% by weight, *Ficus carica* L. 5 to 50% by weight, *Allium cepa* L. 5 to 50% by weight, *Mume Fructus* 0.5 to 10% by weight, *Prunus armeniaca* 1 to 50% by weight, oligosaccharide 5-30% by weight and dietary ingredient 5-30% by weight.

The present invention provides a composition of the health care food beverage for preventing and alleviating intestinal disease comprising the extracts of crude drug wherein radish 5 to 30% by weight, tea leaf 10 to 30% by weight, *Daucus carota* var *sativa* 10 to 20% by weight, *Aurantii nobilis* Pericapium 5 to 10% by weight, *Aurantii immatri* Pericarpium 5 to 10% by weight, *Ficus carica* L. 10 to 20% by weight, *Allium cepa* L. 10 to 20% by weight, *Mume Fructus* 5 to 10% by weight, *Prunus armeniaca* 10 to 20% by weight and dietary ingredient 5-30% by weight.

Above inventive crude drug composition can be added to food and beverage for the preventing and alleviating intestinal disease and constipation.

To develop for health care food, examples of addable food comprising above crude drug composition of the present invention are e.g., various food, beverage, bread, cookies, jam, candy, gum, tea, yogurt, vitamin complex, health improving food and the like, and can be used as power, granule, tablet, chewing tablet, capsule or beverage etc.

Inventive crude drug composition of the present invention has no toxicity and adverse effect therefor; they can be used with safe.

Above described composition therein can be added to food, additive or beverage, wherein, the amount of above described extract in food or beverage may generally range from about 0.01 to 80 w/w % of total weight of food for the health care food composition and 0.02 to 30 g, preferably 0.3 to 5 g in the ratio of 100 ml of the health beverage composition.

Providing that the health beverage composition of present invention contains above described extract as an essential component in the indicated ratio, there is no particular limitation on the other liquid component, wherein the other component can be various deodorant or natural carbohydrate etc such as conventional beverage. Examples of aforementioned natural carbohydrate are monosaccharide such as glucose, fructose etc; disaccharide such as maltose, sucrose etc; conventional sugar such as dextrin, cyclodextrin; and sugar alcohol such as xylitol, and erythritol etc. As the other deodorant than aforementioned ones, natural deodorant such as taumatin, stevia extract such as levaudioside A, glycyrrhizin et al., and synthetic deodorant such as saccharin, aspartam et al., may be useful favorably. The amount of above described natural carbohydrate is generally ranges from about 1 to 20 g, preferably 5 to 12 g in the ratio of 100 ml of present beverage composition.

The other components than aforementioned composition are various nutrients, a vitamin, a mineral or an electrolyte, synthetic flavoring agent, a coloring agent and improving agent in case of cheese chocolate et al., pectic acid and the salt thereof, alginic acid and the salt thereof, organic acid, protective colloidal adhesive, pH controlling agent, stabilizer, a preservative, glycerin, alcohol, carbonizing agent used in carbonate beverage et al. The other component than aforementioned ones may be fruit juice for preparing natural fruit juice, fruit juice beverage and vegetable beverage.

The inventive composition can be used as the mixing agent in the lactic acid bacteria-formulated beverage or paste and the like.

Above-mentioned component can be used independently or in combination.

The present invention provides a health care food comprising about 0.01 to 30 w/w % of the vitamin, oligosaccharides and dietary ingredients besides the crude drug composition of the present invention.

The ratio of the components is not so important but is generally range from about 0.01 to 30 w/w % per 100 w/w % present composition. Examples of addable food comprising aforementioned extract therein are various food, beverage, gum, vitamin complex, health improving food and the like.

The inventive composition may additionally comprise one or more than one of organic acid, such as citric acid, fumaric acid, adipic acid, lactic acid, malic acid; phosphate, such as phosphate, sodium phosphate, potassium phosphate, acid pyrophosphate, polyphosphate; natural anti-oxidants, such as polyphenol,.catechin, α-tocopherol, rosemary extract, vitamin C, licorice root extract, chitosan, tannic acid, phytic acid etc.

It will be apparent to those skilled in the art that various modifications and variations can be made in the compositions, use and preparations of the present invention without departing from the spirit or scope of the invention.

BRIEF DESCRIPTION OF THE DRAWINGS

The above and other objects, features and other advantages of the present invention will more clearly understood from the following detailed description taken in conjunction with the accompanying drawings, in which;

FIG. 1a is for normal control group; FIG. 1b is for loperamide-treated group and FIG. 1c is for KTG075-treated group after loperamide administration;

FIG. 2a is for loperamide-treated group and FIG. 2b is for KTG075-treated group after loperamide administration;

FIG. 3a is for normal control group; FIG. 3b is for KTG075-treated group and FIG. 3c is for loperamide-treated group.

Figure 1A:
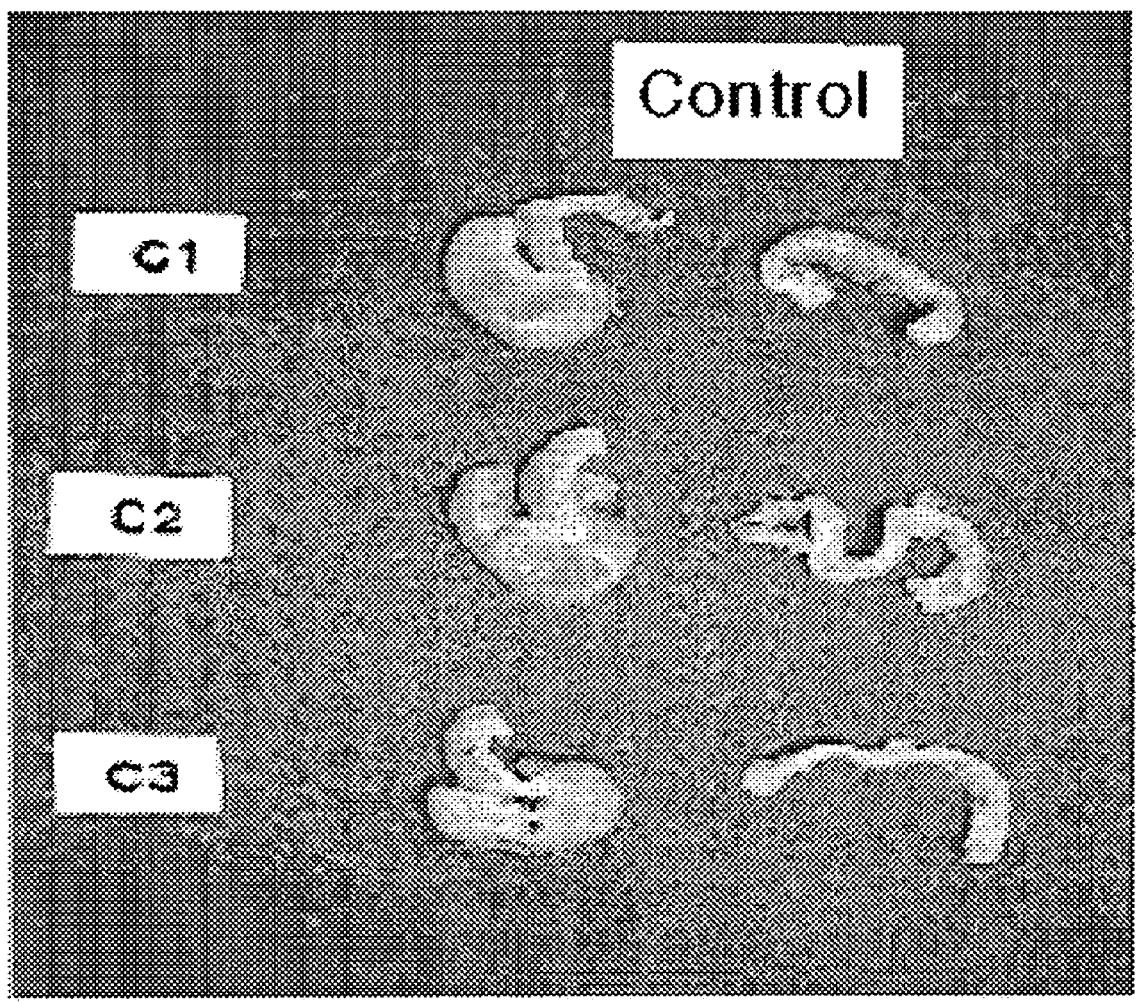
FIG. 1a to 1c show isolated large intestine of each test group.

Hereinafter, the present invention is more specifically explained by the following examples. However, it should be understood that the present invention is not limited to these examples in any manner.

EXAMPLES

The following Examples and Experimental Examples are intended to further illustrate the present invention without limiting its scope.

Example 1

Preparation of Radish (*Raphanus sativus*) Extract 1-1. Preparation 1

100 g of dried *Raphanus sativus* (Hung-nong Seeds Corp., Seoul, Korea) was cut into small pieces, crushed, mixed with 1 L of distilled water and subjected to reflux extraction for 2 hrs at 100° C. to obtain water soluble extract. The extract was filtered with filter paper, concentrated using by vacuum rotary evaporator (Buchi R020, Germany) and dried with freezing dryer to obtain the dried Radish extract.

1-2. Preparation 2

100 g of turnip (*Brassia Lap.*) was cut into small pieces and squeezed to be juice to obtain an extract of turnip.

Each crude extract of Radish and turnip was used as a sample in following Experiment.

Example 2

Preparation of Tea Leaf Extract

Each purchased green tea leaf (Shin-hung Dawon, Hwagae City, Korea), oolong tea leaf (made in Taiwan), Tien-Guan-In tea leaf (made in China), Pu-erh tea leaf (made in China) and black tea leaf (made in SriLanka) was performed by the procedure similar to Example 1-1 and used as a sample in following Experiment.

Example 3

Preparation of Carrot (*Daucus carota* L. var. *sativa* DC.) Extract 100 g of dried carrot (Hung-nong Seeds Corp., Seoul, Korea) or natural carrot was subjected to extraction or treatment by the procedure similar to Example 1-1 or 1-2 to obtain the extract thereof and used as a sample in following Experiment.

Example 4

Preparation of Yellow Mandarin Orange Peel (*Aurantii nobilis* Pericapium) Extract 100 g of yellow mandarin orange peel (Kyung-dong Market, Seoul, Korea) was subjected to extraction by the procedure similar to Example 1-1 to obtain the extract thereof and used as a sample in following Experiment.

Example 5

Preparation of Blue Mandarin Orange Peel (*Aurantii immatri* Pericapium) Extract 100 g of dried blue mandarin orange peel (Kyung-dong Market, Seoul, Korea) was subjected to extraction by the procedure similar to Example 1-1 to obtain the extract thereof and used as a sample in following Experiment.

Example 6

Preparation of Fig (*Ficus carica* L) Extract 100 g of dried *Ficus carica* L. (Samho nonghyup, Seoul, Korea) was subjected to extraction by the procedure similar to Example 1-1 to obtain the extract thereof and used as a sample in following Experiment.

Example 7

Preparation of Onion (*Allium cepa* L.) Extract 100 g of dried *Allium cepa* L. (Hung-nong Seeds Corp., Seoul, Korea) or natural one was subjected to extraction or treatment by the procedure similar to Example 1-1 or 1-2 to obtain the extract thereof and used as a sample in following Experiment.

Example 8

Preparation of Plum (*Mume Fructus*) Extract 100 g of dried *Mume Fructus*. (Kyung-dong Market, Seoul, Korea) was subjected to extraction by the procedure similar to Example 1-1 to obtain the extract thereof and used as a sample in following Experiment.

Example 9

Preparation of Apricot (*Prunus armeniace* L.) Extract 100 g of dried *Prunus armeniace* L. (Samho nonghyup, Seoul, Korea) was subjected to extraction by the procedure similar to Example 1-1 to obtain the extract thereof and used as a sample in following Experiment.

Example 10

Preparation of Crude Drug Combination I

Each extract of radish, green tea leaf, carrot, yellow and blue mandarin orange peel, fig, onion and plum obtained from Example 1 to 9 was mixed together with the ratio shown in Table 1 to obtain their combination mixture. The crude drug combination I group was used as a sample in following Experiment.

TABLE 1

| Group | Crude drug | The ratio of composition (%) |
|---|---|---|
| I | Radish | 30 |
|  | Green tea leaf | 10 |
|  | Carrot | 20 |
|  | Yellow mandarin orange peel | 5 |
|  | Blue mandarin orange peel | 10 |
|  | Fig | 10 |
|  | Onion | 10 |
|  | Plum | 5 |

Example 11

Preparation of Crude Drug Combination II

Each extract of radish, oolong tea leaf, carrot, yellow and blue mandarin orange peel, fig, onion, plum and apricot obtained from Example 1 to 9 was mixed together with the ratio shown in Table 2 to obtain their combination mixture. The crude drug combination II group was designated as "KTG075" hereinafter and used as a sample in following Experiment.

TABLE 2

| Group | Crude drug | The ratio of composition (%) |
|---|---|---|
| II | Radish | 20 |
|  | Oolong tea leaf | 15 |
|  | Carrot | 20 |
|  | Yellow mandarin orange peel | 10 |
|  | Blue mandarin orange peel | 10 |
|  | Fig | 10 |
|  | Onion | 10 |
|  | Plum | 5 |
|  | Apricot | 10 |

Example 12

Preparation of Crude Drug Combination III

Each extract of radish, black tea leaf, carrot, yellow and blue mandarin orange peel, and onion obtained from Example 1 to 9 was mixed together with the ratio shown in Table 3 to obtain their combination mixture. The crude drug combination III group was used as a sample in following Experiment.

TABLE 3

| Group | Crude drug | The ratio of composition (%) |
|---|---|---|
| III | Radish | 20 |
|  | Black tea leaf | 20 |
|  | Carrot | 20 |
|  | Yellow mandarin orange peel | 10 |
|  | Blue mandarin orange peel | 10 |
|  | Onion | 20 |

Example 13

Preparation of Crude Drug Combination IV

Each extract of radish juice, carrot juice, Tien-Guan-In tea leaf, yellow and blue mandarin orange peel obtained from Example 1 to 9 was mixed together with the ratio shown in Table 4 to obtain their combination mixture. The crude drug combination IV group was used as a sample in following Experiment.

TABLE 4

| Group | Crude drug | The ratio of composition (%) |
|---|---|---|
| IV | Radish | 30 |
|  | Tien-Guan-In tea leaf | 20 |
|  | Carrot | 30 |
|  | Yellow mandarin orange peel | 10 |
|  | Blue mandarin orange peel | 10 |

Example 14

Preparation of Crude Drug Combination V

Each extract of radish, black tea leaf, carrot, yellow and blue mandarin orange peel, fig and plum obtained from Example 1 to 9 was mixed together with the ratio shown in Table 5 to obtain their combination mixture. The crude drug combination V group was used as a sample in following Experiment.

TABLE 5

| Group | Crude drug | The ratio of composition (%) |
|---|---|---|
| V | Radish | 15 |
|  | Black tea leaf | 15 |
|  | Carrot | 30 |
|  | Yellow mandarin orange peel | 5 |
|  | Blue mandarin orange peel | 2 |
|  | Fig | 20 |
|  | Plum | 3 |

Example 15

Preparation of Crude Drug Combination VI

Each extract of radish juice, onion juice, carrot juice, Pu-erh tea leaf, yellow and blue mandarin orange peel, fig and plum obtained from Example 1 to 9 was mixed together with the ratio shown in Table 6 to obtain their combination mixture. The crude drug combination VI group was used as a sample in following Experiment.

TABLE 6

| Group | Crude drug | The ratio of composition (%) |
|---|---|---|
| VI | Radish | 20 |
| | Pu-erh tea leaf | 10 |
| | Carrot | 15 |
| | Yellow mandarin orange peel | 10 |
| | Blue mandarin orange peel | 10 |
| | Fig | 10 |
| | Onion | 20 |
| | Plum | 5 |

Example 16

Preparation of Crude Drug Combination VII

Each extract of radish, green tea leaf, carrot, yellow and blue mandarin orange peel, fig, onion, plum and apricot obtained from Example 1 to 9 was mixed together with the ratio shown in Table 7 to obtain their combination mixture. The crude drug combination VII group was used as a sample in following Experiment.

TABLE 7

| Group | Crude drug | The ratio of composition (%) |
|---|---|---|
| VII | Radish | 30 |
| | Green tea leaf | 10 |
| | Carrot | 25 |
| | Yellow mandarin orange peel | 5 |
| | Blue mandarin orange peel | 5 |
| | Fig | 5 |
| | Onion | 10 |
| | Plum | 5 |
| | Apricot | 5 |

Example 17

Preparation of Health Beverage 3000 mg of radish extract prepared in Example 1, 3000 mg of tea extract prepared in Example 2, 2000 mg of carrot extract prepared in Example 3, 100 mg of yellow mandarin orange peel extract prepared in Example 4, 100 mg of blue mandarin orange peel extract prepared in Example 5, 2000 mg of fig extract prepared in Example 6, 200 mg of onion extract prepared in Example 7, 50 mg of plum extract prepared in Example 8, 100 mg of apricot extract prepared in Example 9, 100 mg of citric acid, 100 g of oligosaccharide and 1 g of diet ingredient were mixed and appropriate amount of distilled water was added thereto to make 900 ml of total volume according to the conventional manner well known in the art. The obtained solution was stirred at 85° C. for 1 hr. and filtered. The filtrate was filled in 2 L of sterilized flask, sterilized and kept in refrigerator by conventional health beverage preparation method.

Experimental Example 1

Effect of Crude Drug Combination on Charcoal Meal Transit

To confirm the effect on improvement of intestinal function and constipation, the intestinal transit of charcoal meal was carried out as following procedures.

Male Balb/c mice (Daehan Biolink Co., Eum-sung, Korea) weighing from 24 to 27 grams were used. Eight of mice were divided into control group and 7 test groups respectively.

To examine the effect on intestinal motility, 3.2 mg/ml of crude drug combination prepared in Example 10 to Example 15 was dissolved in water and orally administered for 3 days in test groups. At $4^{th}$ day, test group was fasted with free access to water at 6 p.m. and crude drug combination was administered continually in fasting period.

The control group was prepared by the same method disclosed above except administering water instead of crude drug combination.

Each crude drug combination I~IV was administered at 8 mg (0.2 ml) per animal at 9 a.m. on fifth days. At 60 minutes post dosing, 0.2 ml of charcoal meal consisting of 5 w/w % activated charcoal in 10 w/w % arabic gum (Sigma Co., USA) was administered to each animal.

The animals were sacrificed 30 minutes after charcoal administration.

The intestine was removed and the length of the gut as well as distance of charcoal movement ($R_f$) from the pyloric sphincter to the ilioceacal junction were measured.

As a result of experiment, the test groups showed the increase of intestinal motility of charcoal meal compared to the control group.

Therefore, it is confirmed that each crude drug combination of the present invention was effective to activate intestinal motility, especially the crude drug combination II, KTG075 had an excellent activating activity of intestinal motility compared with other combinations (See Table 8).

TABLE 8

| Group | Increasing rate of movement (%) | Improved order |
|---|---|---|
| Control group | 100.0 | — |
| Crude drug combination I-treated group | 143.7 | 3 |
| Crude drug combination II-treated group | 146.5 | 1 |
| Crude drug combination III-treated group | 142.9 | 4 |
| Crude drug combination IV-treated group | 138.8 | 5 |
| Crude drug combination V-treated group | 145.3 | 2 |
| Crude drug combination VI-treated group | 131.2 | 6 |

Experimental Example 2

Effect of Crude Drug Combination on Constipation

To confirm the effect of inventive composition on improvement of intestinal function and constipation, the following experiment was performed.

To measure the amount of feces, male Sprague-Dawley rat (Daehan Bio link Co., Eum-sung, Korea) weighing from 220 to 240 g were used. All animals were acclimated in a cage for 3 days and divided into 7 groups consisting of 8 to 10 animals.

Animals were given 3 g of feed comprising 1 mg of loperamide (Sigma, USA) from forth days. The control group (loperamide-treated group) was given only water and the test group was administered at the concentration of 3.2 mg/ml crude drug combination dissolved in water until the end of the experiment.

The feces was collected and the weight thereof was measured everyday.

As a result of the experiment to examine the improving effect of each crude drug combination on constipation, it is confirmed that they are effective to increase the feces quantity in each test group during the periods of inducing constipation compared with the control group and especially crude drug composition II, KTG075 showed the excellent effect of improving constipation (See Table 9).

TABLE 9

| | Increase of feces quantity vs. control group (%) Passing days after sample administration | | | | | | | |
|---|---|---|---|---|---|---|---|---|
| Group | D + 1 | D + 2 | D + 3 | D + 4 | D + 5 | D + 6 | D + 7 | D + 8 |
| I | 54* | 31* | 7 | 22 | 19* | 23* | 11 | 4 |
| II | 44* | 64** | 34* | 14 | 31* | 16 | 16 | 30* |
| III | 10 | 53** | 28* | 21 | 1 | 2 | 10 | 12 |
| IV | 19 | 18 | 23* | 19 | 23 | 21 | 9 | 26 |
| V | 2 | 30* | 40** | 42* | 24 | 23 | 51 | 9 |
| VI | 10 | 20 | 30* | 15 | 20 | 18 | 5 | 10 |

D: Day administered sample comprising loperamide.
*p < 0.05,
**p < 0.01

Experimental Example 3

Effect of KTG075 on Constipation

To estimate the effect of KTG075 on constipation, the amount of feces, water content of feces and the intake amount of feed and water were investigated by the modified method disclosed in Experimental Example 2.

In the result, the KTG075 shows the improving effect on constipation in accordance with increasing the freeze-dried feces.

Therefore, it is confirmed that the KTG075 alleviated the constipation so that the appetite, intake of feed and water were increased (See Table 10).

TABLE 10

| | Increase of feces quantity vs. control group (%) Passing days after sample administration | | | | | | | |
|---|---|---|---|---|---|---|---|---|
| Item | D + 1 | D + 2 | D + 3 | D + 4 | D + 5 | D + 6 | D + 7 | D + 8 |
| Feces quantity | 43.9 | 64.4 | 34.1 | 13.8 | 31.5 | 16.5 | 16.2 | 30.5 |
| Dried feces quantity | — | 14.1 | 25.7 | 28.3 | 16.8 | 18.9 | 38.4 | 2.3 |
| Water content in feces | — | 42.6 | 54.2 | 53.8 | 32.2 | 21.3 | 63.6 | 17.3 |
| Intake of feed | 15.3 | 13.6 | 5.9 | 2.6 | 1.5 | 0 | −0.6 | 3.9 |
| Feces quantity/ intake of feed | 28.2 | 41.9 | 27.2 | 7.2 | 35.1 | 9.6 | 15.1 | 13.0 |
| Intake of water | 32.2 | 35.7 | 11.9 | 30.5 | 24.8 | 15.7 | −0.3 | 19.0 |

D: Day administered sample comprising loperamide.
—: No measured

Experimental Example 4

Effect of the KTG075 on Secretion of Mucus

To confirm the effect on improvement of intestinal function related to constipation, the effect of KTG075 on the secretion of mucus was examined.

Mucus of digestive organ plays an important role of protecting an epithelial tissue of intestine from physical damage and chemical stimulus and lubricating intestinal motility. Colonic mucosa is covered with mucus and mucin showing a chemical and physical character of mucus is changed to viscous liquid in alkali. The function of lamina mucosa in colonic mucosa is decreased in case of constipation and if loperamide is administered for a certain period, the thickness of mucus is to be thinned and it acts as a hindrance to the movement of colonic contents.

This experiment was carried out according to the modified method disclosed in Experimental Example 2. The intestine of animal from cecum to the rectum was removed, fixed with 10% formaldehyde in phosphate buffer and the number of the feces pellet in large intestine duct was counted.

As a result of experiment, the number of the feces pellet of control group was 5.5 on the average, however that of KTG075-treated group was 1.75 with 68.2% decreased ratio (See Table 11).

Figure 1B:
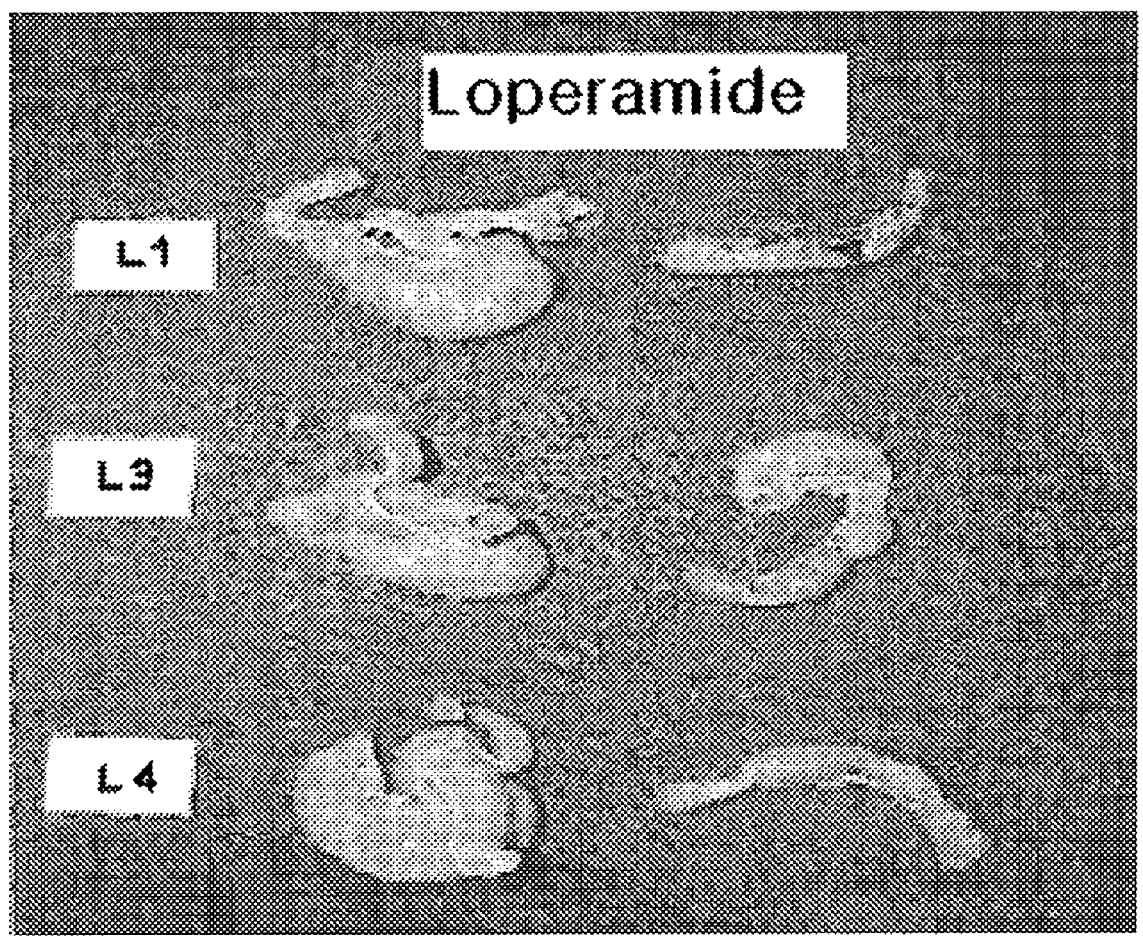
Figure 1C:
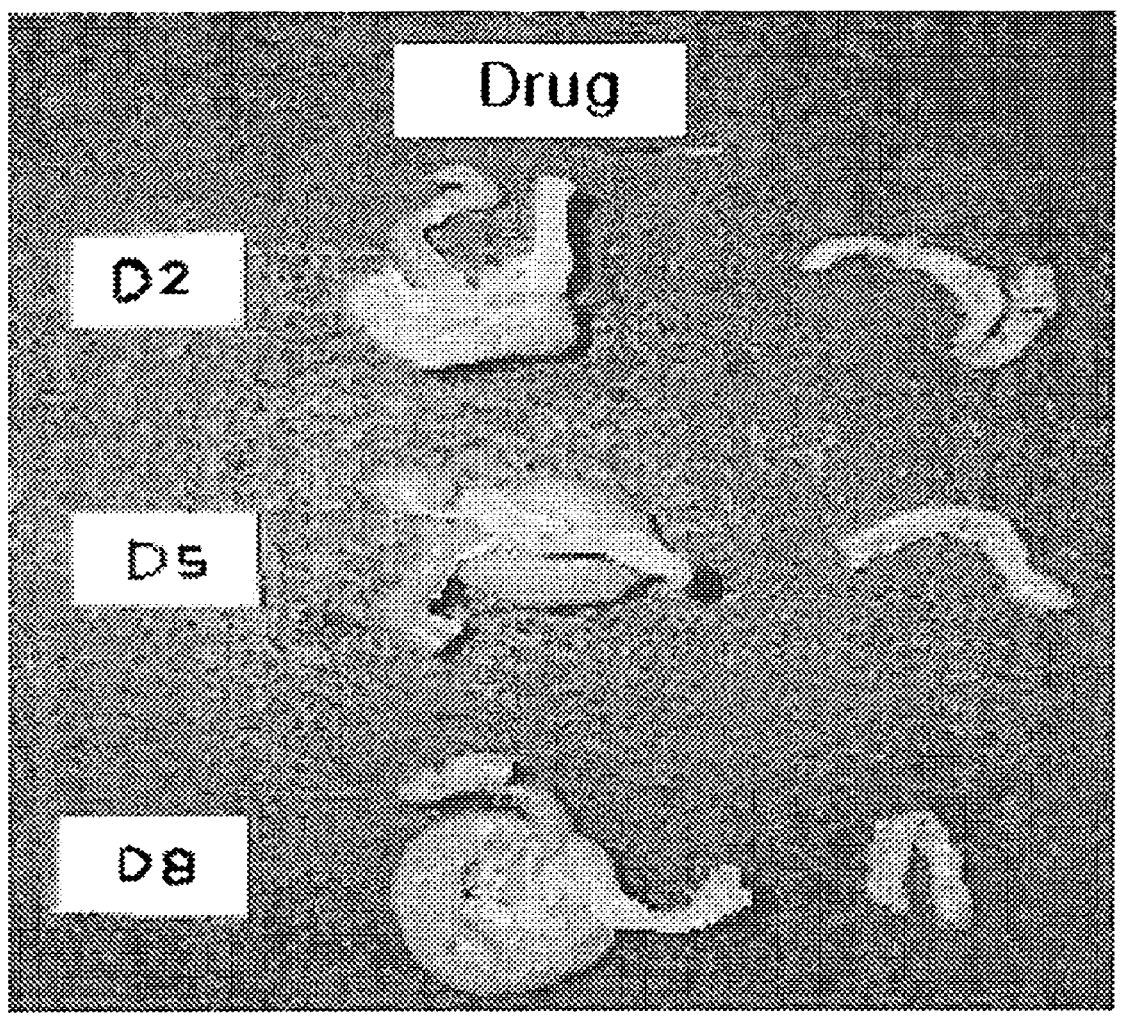

Also, the residue in the cecum and rectum was not observed in the normal group and the KTG075-treated group, while a lot of residue was observed in control group as shown in FIG. 1a to 1c.

Therefore, it is confirmed that the KTG075 had an excellent anti-constipation effect with the consistent result in respect to the feces quantity and feces pellet in the large intestine.

Also, the mucus secreting-cell and the lamina mucus were observed by a substantial examination to estimate the secretion of mucus in the intestine.

Figure 2A:
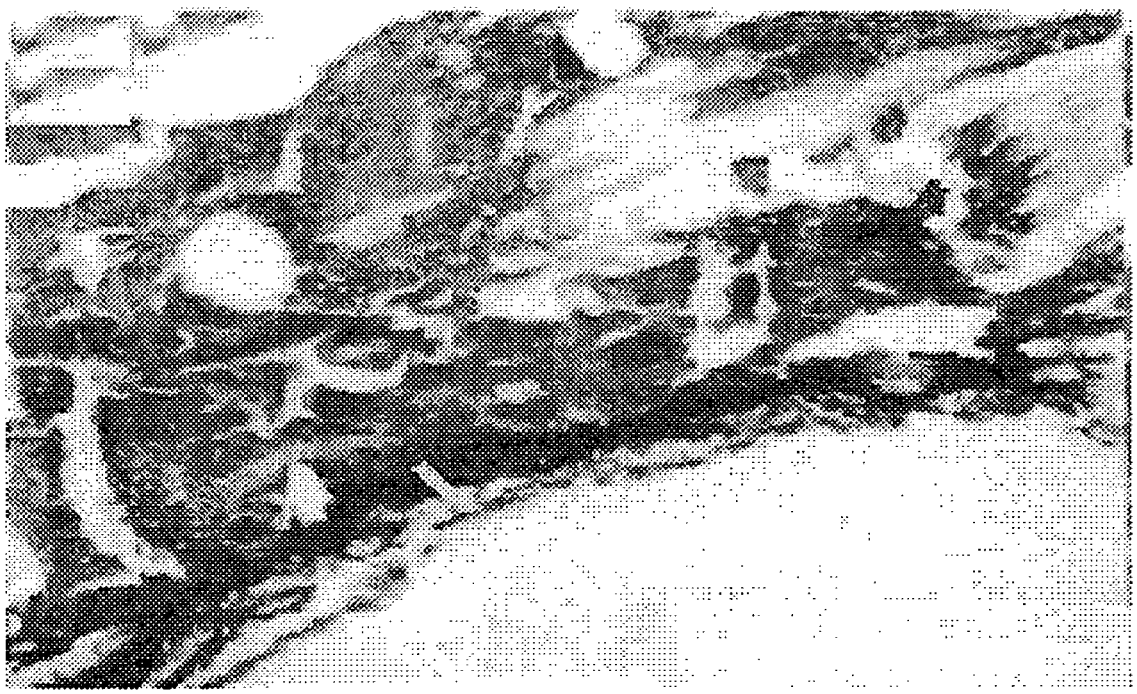
FIG. 2a and 2b show the thickness of the mucus tissue.
Figure 2B:
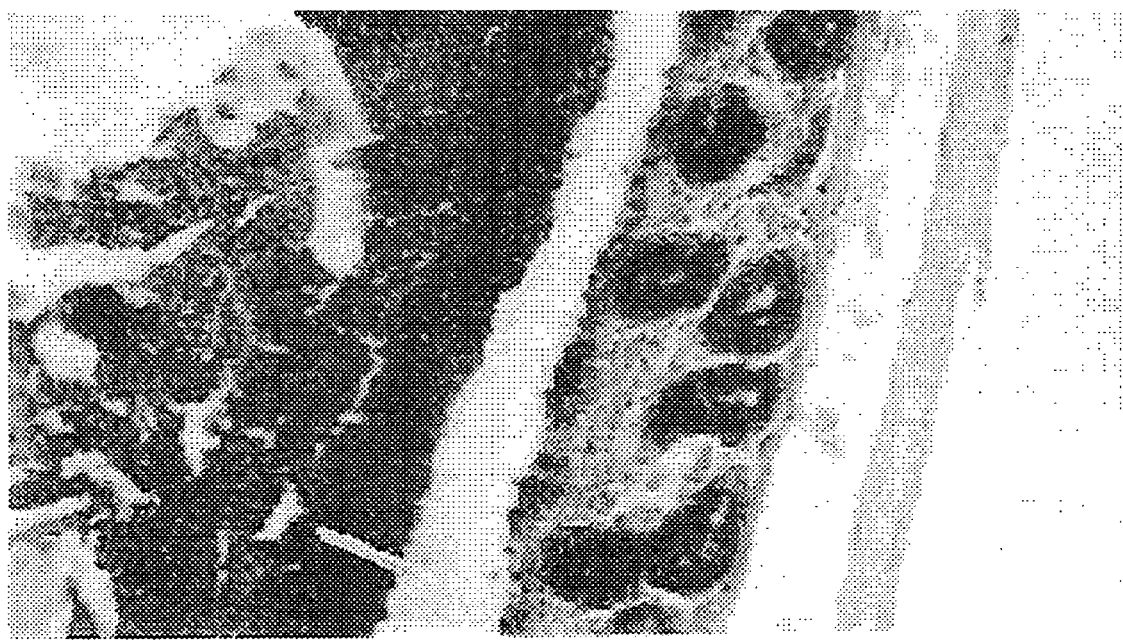

As shown in FIGS. 2a and 2b, KTG075-treated group showed that the mucus secretion was activated and the thickness of mucus was apparently increased compared with the constipation-induced group.

The mucus thickness of constipation-induced group was 11.9 μm with 31% decrease compared with 17.2 μm of the normal group, but the KTG075-treated group showed similar mucus thickness of 17.4 μm to the normal group (See Table 12).

At the result, it is verified that the KTG075 was effective to alleviate the constipation by increasing the mucus and the motility of the intestine.

TABLE 11

| | Group | |
|---|---|---|
| | Control group | KTG075-treated group |
| No. of feces pellet | 5.5 | 1.75 |

TABLE 12

| Group | Thickness of mucus (μm) | Increasing rate vs. normal group (%) |
|---|---|---|
| Normal group | 17.2 ± 3.24[1] | 100 |
| Control group | 11.9 ± 2.49** | 69.2 |
| KTG075-treated group | 17.4 ± 5.55$$ | 101.2 |

[1]means ± standard deviation,
**normal group vs. p < 0.01,
$$Control group vs. p < 0.01

Reference Example

Culture Media

BCP agar medium (Eiken, Japan) used in the following experiment was prepared by adding yeast extract 2.5 g, peptone 5 g, glucose 1 g, L-cystein 0.1 g, bromcresol purple 0.04 g and agar 15 g/liter.

NB (nutrient broth, Difco) was prepared by adding beef extract 3 g and peptone 5 g/liter and adjusting to the pH 6.8.

NA (nutrient agar, Difco) was prepared by adding beef extract 3 g, peptone 5 g and agar 15 g/liter.

MRS (Mann-Rogosa-Sharpe, Difco) broth was prepared by adding 10 g of proteose peptone, 10 g of beef extract, 10 g of yeast extract, 20 g of dextrose, 1 g of tween-80, 2 g of triammonium citrate, 5 g of sodium acetate, 0.1 g of MgSO$_4$.7H$_2$O, 0.05 g of MnSO$_4$.4H$_2$O and 2 g/liter of K$_2$HPO$_4$, and adjusting to the pH 6.0~6.5.

MRS agar medium was prepared by adding 1.2~1.5% agar to above MRS broth. As it was used in anaerobic condition, 0.05% L-cysteine was added thereto.

Experimental Example 5

Effect of KTG075 on the Number of Intestinal Bacteria 5-1. Animal Preparation

Male Sprague Dawley rats weighing 220~240 g were maintained in a controlled environment with the temperature at 22° C.-24° C. and the humidity at 60%-80% with 12 hours of light and dark cycles for 6 days prior to use.

For the constipation induction, loperamide (Signa Co.) mixed with 1 mg per 3 g feed was administered to the SD rats from 7$^{th}$ day.

Normal control group and loperamide-administered group was only provided with water and KTG075-administered group was provided with 7 mg/ml KTG075.

Feces of each group was collected everyday to measure the number of viable colonies.

5-2. The Measurement of Viable Colonies 1 g of feces was suspended in 100 ml of saline (if anaerobic condition: 0.05% L-cysteine added) and orderly diluted to the range of $10^{4-8}$.

Diluted samples were spread on NA plates and incubated for 7 days at 37° C. in aerobic/anaerobic condition (H$_2$-5%: CO$_2$-15%:N$_2$-80%, Mart AJ9028 chamber and Anoxomat WS8000, Netherland) and growing colonies were counted and expressed as c.f.u. (Colony forming units/g wet feces).

Figure 3A:
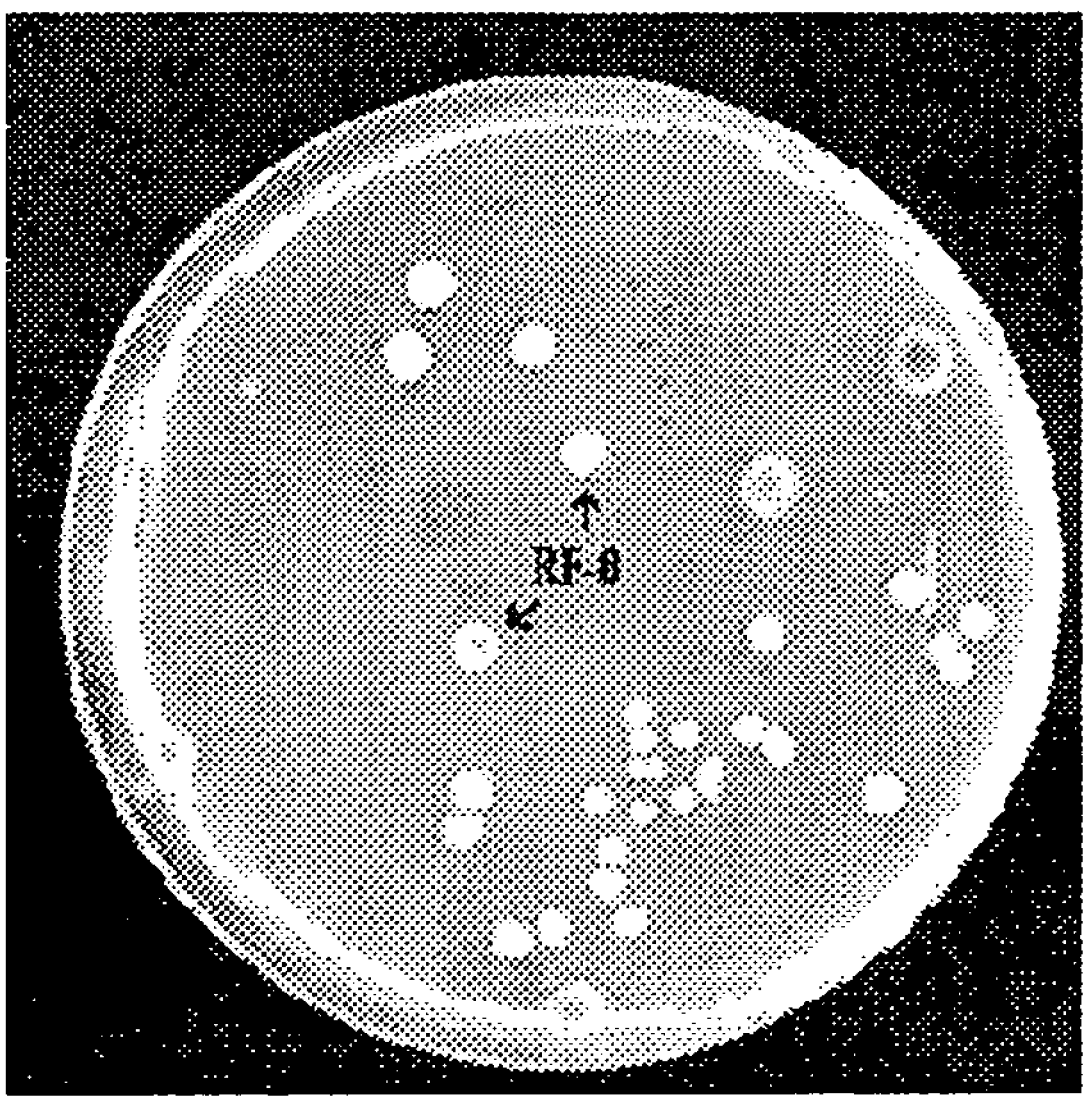
FIG. 3a to 3c show the culture plates of each test group 2 days after KTG075 administration.
Figure 3B:
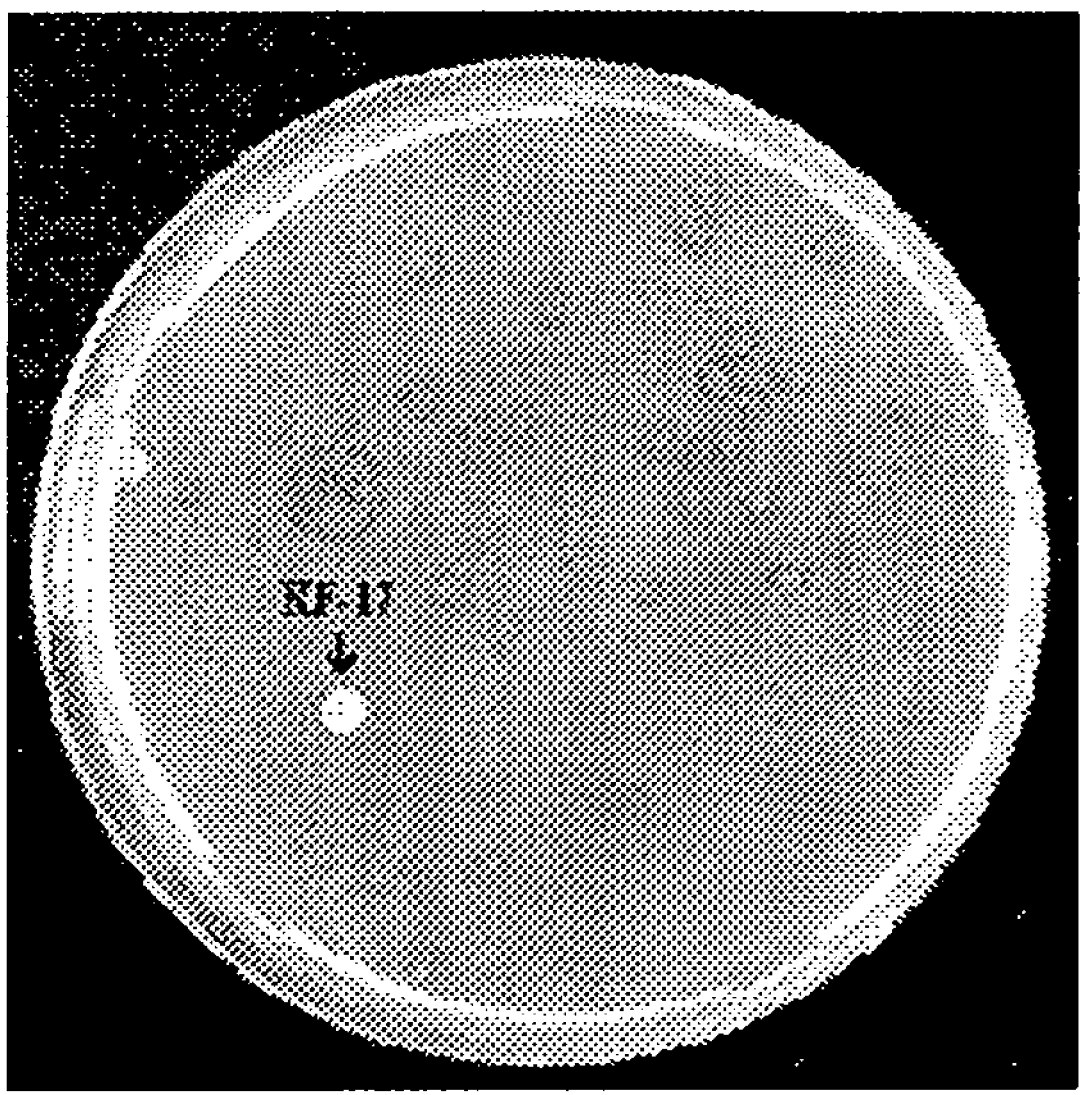
Figure 3C:
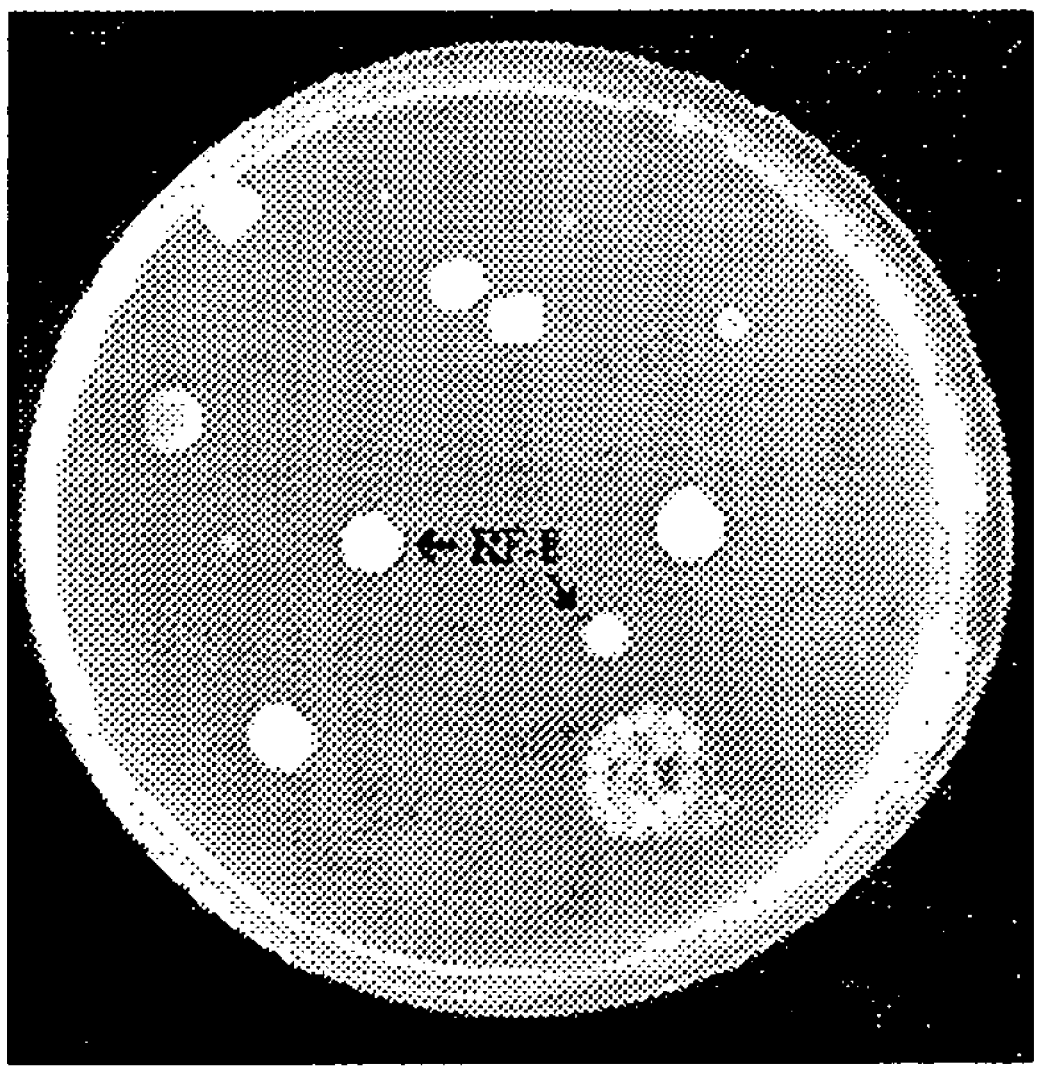

FIGS. 3$a$, 3$b$ and 3$c$ are pictures of $10^7$-diluted plates at 2 days after KTG075 (D+2 day) administration. FIG. 3$a$ is for normal group; FIG. 3$b$ is for KTG075-treated group and FIG. 3$c$ is for loperamide-administered group.

Punctiform and translucent colonies of lactic acid bacteria were grown on solid medium at 1 week after KTG075 treatment and various 2~5 mm milky-white opaque colonies were also observed. The number of colonies on the plate of KTG075-treated group was much less than that of normal or loperamide-treated group.

The result of colony counts (c. f. u.) was shown in Table 13.

In view of total counts, there was little difference among normal, loperamide-treated and KTG075 treated group.

After KTG075 treatment, it was observed that the total count in aerobic condition was somewhat decreased at D+2 day to D+4 day and it means that the growth of aerobic bacteria can be inhibited by KTG075.

TABLE 13

| Group | Condition | D + 2 day | D + 4 day |
|---|---|---|---|
| Normal group | Aerobic | $2.9 \times 10^8$–$2.7 \times 10^9$ | $2.2 \times 10^8$–$1.3 \times 10^9$ |
| | Anaerobic | $2.5$–$4.2 \times 10^9$ | $1.7$–$3.3 \times 10^9$ |
| KTG075-treated group | Aerobic | $2.2$–$7.5 \times 10^8$ | $4.7$–$8.7 \times 10^8$ |
| | Anaerobic | $3.4$–$6.9 \times 10^9$ | $5.1$–$6.9 \times 10^9$ |
| Loperamide-treated group | Aerobic | $2.9 \times 10^8$–$1.2 \times 10^9$ | $3.2 \times 10^8$–$1.5 \times 10^9$ |
| | Anaerobic | $4.3$–$4.9 \times 10^9$ | $3.2$–$9.1 \times 10^9$ |

On the plate of D+2 day, punctiform and translucent lactic acid bacteria colonies were well grown while other opaque and milky-white colonies were not (See FIG. 3$a$ to 3$c$).

Among those bacteria, the dominant bacteria was separated and identified by MIDI system to examine the effect of KTG075 on the growth of intestinal bacteria in vitro.

5-3. Separation of Dominant Bacteria and Identification of Separated Strain

The cultures were grown for 3 days on NA plates and/or for 7 days on BCP agar plates. Identification of separated strain was performed according to MIDI (microbial identification system, Microbial ID, Inc., Newark, Del.), which can analyze the sort and distribution of cellular fatty acid.

According to the MIDI standard method, methyl ester of fatty acid was prepared and the extract thereof was analyzed by Gas Chromatography (Hewlett-Packard, silica) equipped with capillary column (HP19091B-102, 25 m×0.2 mm). And the distribution of fatty acid was analyzed by chromatopac C-R 4A data analyzer.

The results are shown in Table 14 and 15. RF no. means the number of strain isolated from the feces of rat in above experiment.

TABLE 14

| RF No. | Colony morphology | Cellular fatty acids | Identified as |
|---|---|---|---|
| 1 | Milky-white, irregular, umbonate, undulate, dull, 2 mm in diam. on NA | Table 15 | *Streptococcus sanguis* |
| 5 | Punctiform, raised, entire, smooth, translucent, on BCP agar | Table 15 | *Lactobacillus delbrueckii* |
| 8 | White, irregular, umbonate, undulate, concentric, opaque, 5 mm in diam. on NA | Table 15 | *Klebsiella pneumoniae* |
| 11 | White, circular, flat, entire, smooth, opaque, 3 mm in diam. on NA | Table 15 | *Brevibacillus brevis* |
| 12 | Punctiform, raised, entire, smooth, translucent, on BCP agar | Table 15 | *Lactobacillus helveticus* |
| 17 | Yellow, circular, pulvinate, entire, contoured, opaque, 3 mm in diam. on NA | Table 15 | *Dermacoccus nishinomiyaensis* |

TABLE 15

| RF No. | 10:0 | 12:0 | 13:0 | 13:0 iso | 14:0 | 14:0 iso | 14:1 w5c | 15:0 | 15:0 iso | 15:0 ante-iso | 15:1 w6c |
|---|---|---|---|---|---|---|---|---|---|---|---|
| 1 | — | 1.02 | — | — | 22.85 | — | — | — | — | — | — |
| 5 | 0.84 | 6.28 | 0.67 | — | 18.82 | — | — | — | — | — | — |

TABLE 15-continued

| | | | | | | | | | | |
|---|---|---|---|---|---|---|---|---|---|---|
| 8 | — | 5.25 | 0.37 | — | 10.95 | — | — | 1.33 | — | — | — |
| 11 | — | — | — | 0.29 | 0.28 | 2.00 | — | — | 30.17 | 52.24 | — |
| 12 | 2.57 | 3.81 | — | — | 3.11 | — | 1.75 | — | — | — | — |
| 17 | — | — | — | — | 0.50 | — | — | 1.56 | 7.34 | 0.33 | 2.09 |

| RF No. | 16:0 | 16:0 iso | 16:1 isoH | 17:0 | 17:0 iso | 17:0 cyclo | 17:0 ante-iso | 17:0 10-met | 17.1 w8c | 17:1 iso w9c |
|---|---|---|---|---|---|---|---|---|---|---|
| 1 | 42.61 | — | — | — | — | — | — | — | — | — |
| 5 | 10.31 | — | — | — | — | — | — | — | — | — |
| 8 | 27.99 | — | — | 0.39 | — | 18.94 | — | — | — | — |
| 11 | 1.02 | 2.29 | — | — | 5.34 | — | 4.08 | — | — | — |
| 12 | 14.59 | — | — | — | — | — | — | — | — | — |
| 17 | 2.83 | 2.23 | 0.82 | 2.83 | 15.15 | — | 2.41 | 2.26 | 26.74 | 14.43 |

| RF No. | 17:1 ante-iso w9c | 18:0 | 18:0 iso | 18:1 w7c | 18:1 w9c | 19:0 | 19:0 iso | 19:0 cyclo w8c | 20:0 | 20:1 w9c |
|---|---|---|---|---|---|---|---|---|---|---|
| 1 | — | 2.31 | — | 9.11 | — | — | — | 16.44 | — | — |
| 5 | — | 1.76 | — | 1.60 | 56.48 | — | — | — | — | 3.25 |
| 8 | — | 0.18 | — | 12.16 | — | — | — | 2.26 | — | — |
| 11 | — | 0.83 | 0.20 | — | — | — | 0.63 | — | 0.43 | — |
| 12 | — | — | — | — | 49.50 | — | — | — | — | — |
| 17 | 0.91 | — | — | 0.64 | 6.24 | — | — | — | — | — |

Experimental Example 6

Effect of KTG075 on the Growth of Intestinal Bacteria

To examine the effect of KTG075 on the growth of intestinal bacteria, beneficial bacteria and harmful bacteria strain was cultured in KTG075 containing-optimum medium.

Lactic acid bacteria such as *lactobacillus* and *bifidobacterium* was cultured in MRS broth (containing 0.05% L-cysteine) and other strains were cultured NB broth.

100 μl of preculture solution of each strain was inoculated 10 ml of NB or MRS broth in 15 ml corning culture tube and incubated at 37° C. for 72 hours. Test group was treated at the concentration of 7,000 μg/ml KTG075 and lactic acid bacteria was cultured under anaerobic condition ($H_2$-5%: $CO_2$-15%:$N_2$-80%, Mart AJ9028 chamber and Anoxomat WS8000, Netherland).

After incubation, the number of viable bacteria of KTG075 containing media was compared with that of normal group. The viable count was expressed as the number of viable bacteria per 1 ml. Test strain was comprised of *Bifidobacterium bifidum* (KCTC 3442), *Bifidobacterium longum* (KCTC 3128), *Lactobacillus casei* 160, *Lactobacillus delbrueckii* RF-5, *Lactobacillus helveticus* RF-12, *Escherichia coli*, *Proteus vulgaris*, *Salmonella typimurium*, *Staphylococcus aureus*, *Yersinia enterocolityca* and *Klebsiella pneumonia* RF-8.

As shown in Table 16, beneficial bacteria such as *Lactobacillus casei*, *Lactobacillus helveticus*, *Bifidobacterium bifidum* and *Bifidobacterium longum* were not affected by KTG075 treatment at their growth.

However, the growth of harmful bacteria such as *Salmonella typimurium*, *Proteus vulgaris*, *Yersinia enterocolityca* and *Klebsiella pneumonia* were inhibited by KTG075 treatment.

TABLE 16

| Strain | Control | KTG075 7,000 μg/ml | Effect |
|---|---|---|---|
| *Salmonella typimurium* | 1.9–3.8 × $10^8$ | Below 1 × $10^6$ | Inhibition |
| *Proteus vulgaris* | 3.0–5.7 × $10^8$ | 8.8 × $10^7$ | Inhibition |
| *Yersinia enterocolityca* | 3.2–4.5 × $10^8$ | Below 1 × $10^4$ | Inhibition |
| *Escherichia coli* | 1.4 × $10^8$ | 1.5 × $10^8$ | — |
| *Klebsiella pneumonia* RF-8 | 5.6 × $10^8$ | Below 3.5 × $10^7$ | Inhibition |
| *Lactobacillus casei* 160 | 1.8–6.1 × $10^8$ | 6.5 × $10^8$ | — |
| *Lactobacillus helveticus* RF-12 | 1.1 × $10^8$ | 1.1 × $10^8$ | — |
| *Bifidobacterium bifidum* (KCTC 3442) | 2.0 × $10^7$ | 1.0 × $10^7$ | — |
| *Bifidobacterium longum* (KCTC 3128) | 3.8 × $10^8$ | 1.4 × $10^8$ | — |

Experimental Example 7

Toxicity Test

To examine the toxicity of the KTG075 prepared to Example 11, repetitive toxicity tests were performed on mouse.

The ICR mice (25±2 g, Jung-Ang Lab Animal Inc.) and Sprague Dawley rats (200±20 g, Jung-Ang Lab Animal Inc.) were divided into 9 groups per 10 animals and the inventive KTG075 was administered to the mice and rats at 1000, 5000 mg/kg for 1, 2 or 3 months with potable water.

As the result, there was no death example of the animals administered with inventive KTG075 and there was no significant abnormality in the gain of weight, the caloric intake of feed, the hematological analysis or the histological test etc. In accordance with above results, it was confirmed that the KTG075 was safe.

Experimental Example 8

Clinical Test

The KTG075 showing the great effect on constipation in animal model was administered to four patients suffering from constipation symptom at 2 g/l time for 1, 2 or 3 months and the effect on constipation was monitored.

As a result of experiment, constipation symptom was improved in all patients ingesting the KTG075. Therefore, it could be confirmed that the KTG075 was effective to improve constipation and intestinal function (Table 17).

TABLE 17

| SEX | Constipation symptom | The secondary symptom | The method of ingestion | Effect |
|---|---|---|---|---|
| Female (23 years old) | 1~2 times/week evacuation Excess force for evacuation Remaining feeling of feces | Severe pimple Discomfort with intestine | 2 times/day in 1st month Once a day in 2nd month 1~2 times/week in 3rd month | 3 days after administration, large amount of evacuation Change of the feces color from black to brown Decrease of the hardness of feces Lessen remaining feeling of feces and discomfort with intestine |
| Female (36 years old) | 1~2 times/week evacuation Excess force for evacuation Remaining feeling of feces | Discomfort with intestine loss of appetite | 2 times/day in 1st month Once a day in 2nd month | 5 days after administration, large amount of evacuation Change of the feces color from black to brown Decrease of the hardness of feces Lessen remaining feeling of feces and discomfort with intestine |
| Female (22 years old) | 1~2 times/week evacuation Excess force for evacuation Remaining feeling of feces | Difficulty in evacuation in spite of intake of conventional laxatives | 2 times/day in 1st month Once a day in 2nd month | 3 days after administration, large amount of evacuation 1 month after administration, the problems of constipation decreased 2 month after administration, constipation symptom disappeared and administration quitted |
| Female (33 years old) | 1~2 times/week evacuation Excess force for evacuation Remaining feeling of feces | Low efficacy of drug for treating conventional laxatives Severe pimple | 3 times/day in 1st month 2 times/day in 2nd month | Gas formation during first 5 days 5 days after administration, large amount of evacuation Evacuation once a day with lessening discomfort with intestine |

Hereinafter, the formulating methods and kinds of excipients will be described, but the present invention is not limited to them. The representative preparation examples were described as follows.

Preparation of Suppository

| KTG 075 | 75 g |
|---|---|
| Tetrahydrozoline Hydrochloride | 1 g |
| Lidocaine | 60 g |
| Hydrocortisone Acetate | 5 g |
| Allantoin | 20 g |
| Tocopherol Acetate | 60 g |
| Soft silica | 20 g |
| Pharmazol B115 | 1409 g |

Melted pharmazol B115 at 50~70° C. was stirred at room temperature, serially dispersed and cooled down at 40° C. The preparation was prepared by filling suppository with above suspension, freezing and forming by conventional suppository preparation method.

Preparation of Tablet

| KTG075 | 100 mg |
|---|---|
| Corn Starch | 100 mg |
| Lactose | 100 mg |
| Magnesium Stearate | 2 mg |

Tablet preparation was prepared by mixing above components and entabletting.

Preparation of Capsule

| KTG075 | 100 mg |
|---|---|
| Corn starch | 100 mg |
| Lactose | 100 mg |
| Talc | 2 mg |
| Magnesium Stearate | optimum amount |

Tablet preparation was prepared by mixing above components and filling gelatin capsule by conventional gelatin preparation method.

Preparation of Liquid

| KTG075 | 100 mg |
|---|---|
| Sugar | 20 g |

-continued

| | |
|---|---|
| Fructose | 20 g |
| Lemon flavour | optimum amount |
| Distilled water | 100 ml |

Liquid preparation was prepared by mixing above components and then filling 100 ml brown bottle sterilizing by conventional liquid preparation method.

Preparation of Health Care Food

| | |
|---|---|
| KTG075 | 1000 mg |
| Vitamin mixture | 20 g |
| Vitamin A acetate | 70 μg |
| Vitamin E | 1.0 mg |
| Vitamin $B_1$ | 0.13 mg |
| Vitamin $B_2$ | 0.15 mg |
| Vitamin B6 | 0.5 mg |
| Vitamin B12 | 0.2 μg |
| Vitamin C | 10 mg |
| Biotin | 10 μg |
| Amide nicotinic acid | 1.7 mg |
| Folic acid | 50 μg |
| Calcium pantothenic acid | 0.5 mg |
| Mineral mixture | optimum amount |
| Ferrous sulfate | 1.75 mg |
| Zinc oxide | 0.82 mg |
| Magnesium carbonate | 25.3 mg |
| Monopotassium phosphate | 15 mg |
| Dicalcium phosphate | 55 mg |
| Potassium citrate | 90 mg |
| Calcium carbonates | 100 mg |
| Magnesium chloride | 24.8 mg |

The above-mentioned vitamin and mineral mixture may be varied in many ways. Such variations are not to be regarded as a departure from the spirit and scope of the present invention.

Preparation of Health Beverage

| | |
|---|---|
| KTG075 | 1000 mg |
| Citric acid | 100 mg |
| Oligosaccharide | 100 g |
| Apricot concentration | 2 g |
| Taurine | 1 g |
| Distilled water | 900 ml |

Health beverage preparation was prepared by dissolving active component, mixing, stirred at 85° C. for 1 hour, filtered and then filling all the components in 2000 ml ample and sterilizing by conventional health beverage preparation method.

Preparation of Yogurt

| | |
|---|---|
| KTG075 | 10 w/w % |
| Non-fat milk | 12 w/w % |
| Glucose | 4 w/w % |
| Sucrose | 2 w/w % |
| Betacyclodextrin | 1 w/w % |
| Water | 70 w/w % |

Above components were mixed, homogenized and heated for 10 minutes at 85 ~90° C. And then cooled mixture was inoculated with 1 w/w % of lactic acid bacteria strain and subsequently incubated for 8 hours at constant 50° C.

For one's favor, 8 w/w % of fruit preserve or jam made from banana, strawberry, pitch, kiwi and so on, 0.07 w/w % of yogurt flavor can be mixed to prepare the fermented food.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims

What is claimed is:

1. A health care food comprising an extract as an active ingredient including *Raphanus sativus* L., oolong tea leaf, *Daucus carota* var *sativa, Aurantii nobihs* Pericapium, *Aurantii immatri* Pericapium, *Ficus carica* L., *Allium cepa* L., *Mume Fructus* and *Prunus armeniaca*, together with a sitiologically acceptable additive in an effective amount thereof for treating and alleviating constipation and intestinal disease caused by microorganisms.

2. The food of claim 1, wherein the health care food comprising the extract as the active ingredient including *Raphanus sativus* L., oolong tea leaf, *Daucus carota* var *sativa, Aurantii nobilis* Pericapium, *Aurantii immatri* Pericarpium, *Ficus carica* L., *Allim cepa* L., *Mume Fructus* and *Prunus armeniaca* is in a ratio of 1-2:0.1-1:1-2:0.01-1:0.01-1:0.01-1:0.1-2:0.01-1:0.01-1.

* * * * *